United States Patent [19]

Rule et al.

[11] Patent Number: 4,792,641

[45] Date of Patent: Dec. 20, 1988

[54] PROCESS FOR PREPARING IODINATED AROMATIC COMPOUNDS

[75] Inventors: Mark Rule; Donald W. Lane; Thomas H. Larkins; Gerald C. Tustin, all of Kingsport, Tenn.

[73] Assignee: Eastman Kodak Company, Rochester, N.Y.

[21] Appl. No.: 29,899

[22] Filed: Mar. 25, 1987

[51] Int. Cl.⁴ .................. C07C 17/12; C07C 17/24
[52] U.S. Cl. .................................. 570/202; 570/206
[58] Field of Search .................. 570/202, 203, 206; 270/204

[56] References Cited

U.S. PATENT DOCUMENTS

| | | | |
|---|---|---|---|
| 3,363,010 | 1/1968 | Schwarzenbek | 570/203 |
| 4,368,339 | 1/1983 | Tada et al. | 570/202 |
| 4,650,915 | 3/1987 | Arpe | 570/202 |

FOREIGN PATENT DOCUMENTS

| | | | |
|---|---|---|---|
| 0164045 | 12/1985 | European Pat. Off. | 570/202 |
| 0181790 | 4/1986 | European Pat. Off. | 570/206 |
| 0183579 | 6/1986 | European Pat. Off. | 570/203 |
| 3334673 | 4/1985 | Fed. Rep. of Germany | 570/202 |
| 3420706 | 12/1985 | Fed. Rep. of Germany | 570/202 |
| 0077631 | 5/1982 | Japan | 570/206 |
| 0002358 | 4/1988 | World Int. Prop. O. | 570/203 |

*Primary Examiner*—Werren B. Lone
*Attorney, Agent, or Firm*—Charles R. Martin; William P. Heath, Jr.

[57] ABSTRACT

The invention relates to a process for isomerizing and transiodinating iodoaromatic compounds over a non-acid catalyst.

13 Claims, No Drawings

PROCESS FOR PREPARING IODINATED AROMATIC COMPOUNDS

BACKGROUND OF THE INVENTION

1. Field of the Invention

The present invention relates to processes for iodinating aromatic compounds over non-acid catalysts wherein undesired isomers are recycled across a catalyst to effect isomerization and transiodination.

2. Discussion of Background

It has long been desired to be able to derivatize aromatic compounds and in particular condensed ring aromatic compounds in commercially attractive quantities since many of these compounds possess properties which would fill long sought needs. In particular, the compound 2,6-naphthalene dicarboxylic acid or its esters is particularly desired for use in the manufacture of polyesters which would have excellent barrier properties when fabricated into films, bottles or coatings. However, known techniques for producing 2,6-naphthalene dicarboxylic acid and esters are very expensive and impractical for commercial exploitation.

3. Description of the Prior Art

Synthesis of iodobenzene starting from benzene and iodine is usually carried out in the liquid phase in the presence of an oxidative agent, preferably nitric acid. Such techniques have been described in the literature and in particular in Japanese No. 58/77830, U.S.S.R. Pat No. 453392 and by Datta and Chatterjee in the *Journal of the American Chemical Society*, 39, 437, (1917). Other oxidative agents have also been suggested but none of these have proven to be more efficient or convenient than nitric acid. Typical of the other oxidative agents which have been suggested are iodic acid, sulfur trioxide and hydrogen peroxide as described by Butler in the *Journal of Chemical Education*, 48, 508, (1971). The use of metal halogenides to catalyze iodination has been suggested by Uemura, Noe, and Okano in the *Bulletin of Chemical Society of Japan*, 47, 147, (1974). The concept of direct iodination of benzene in the gas phase over the zeolite 13X has been suggested in Japanese Patent Publication No. 82/77631 in the absence of any oxidizing agent.

Ishida and Chono in Japanese Kokai No. 59/219241 have suggested a technique for oxyiodinating benzene over very acidic zeolite catalyst having a silica to alumina ($SiO_2:Al_2O_3$) ratio of greater than 10. In this technique benzene is reacted with iodine in the presence of oxygen to produce iodinated benzene. According to this disclosure approximately 96% of the benzene which is converted is converted to iodinated form. However, the remaining benzene is oxidized to carbon dioxide and other combustion products resulting in the loss of valuable starting material.

OTHER INFORMATION

Subsequent to the present invention, Paparatto and Saetti disclosed in European Patent Application Nos. 181,790 and 183,579 techniques for oxyiodination of benzene over zeolite catalysts. European Patent Application No. 181,790 suggests the use of ZSM-5 and ZSM-11 type zeolites which have been exchanged prior to use with the least one bivalent or trivalent cation. According to this disclosure the utilization of these zeolites in the acid or alkaline form results in a rapid decrease in catalytic activity in relatively few hours. European Patent Application No. 183,579 suggests the utilization of X type or Y type of zeolite in non-acid form. According to No. 183,579 the X or Y zeolites have to be used in the form exchanged with monovalent bivalent or trivalent cations and in particular with alkaline or rare earth cations. The techniques of Nos. 181,790 and 183,579 prepare the monoiodobenzene in selectivities in excess of 90% and only distinctly minor amounts of the diiodobenzene compounds.

There is presently no effective means of converting undesired isomers produced in these processes into specifically desired isomers either by multi-step reaction or isomerization processes. Heretofore, isomerization of haloaromatic compounds has been considered a difficult process, requiring strongly acidic catalyst and long reaction times.

Accordingly, a need exists for a process by which undesired iodoaromatic isomers can be easily and economically isomerized to desired isomeric products.

RELATED APPLICATIONS

Copending applications Ser. Nos. 912,806, filed Sept. 29, 1986, 029,959 filed Mar. 25, 1987, and 029,898 filed Mar. 25, 1987 disclosed techniques for iodinating aromatic compounds over non-acid catalysts. The selectivities of these techniques to the desired products is improved by conducting the techniques of comparatively low temperatures on the order of from about 100° C.–250° C. and using an oxidation catalyst. However, even under these conditions undesired isomers are produced in these processes.

BRIEF DESCRIPTION OF THE INVENTION

Accordingly, one object of the present invention comprises a technique for isomerizing an iodoaromatic compound over a non-acid catalyst to effect transiodination to desired isomers.

Another object of the present invention comprises a technique for isomerizing iodoaromatics produced in an oxyiodination reaction.

These and further objects of the present invention which will become apparent from the following disclosure have been attained by a process which comprises reacting iodoaromatic compounds over a non-acid catalyst to effect isomerization and/or transiodination.

DESCRIPTION OF THE PREFERRED EMBODIMENTS

The aromatic compounds which can be utilized in the practice of the present invention are essentially any aromatic compound including substituted and unsubstituted aromatics. Suitable aromatic compounds include hydrocarbon aromatics, nitrogen containing aromatics and sulfur containing aromatics. Typical hydrocarbon aromatics include benzene and biphenyl, condensed ring aromatics such as naphthalene and anthracene, sulfur containing aromatics including thiophene and benzothiophene, nitrogen containing aromatics such as pyridine and benzopyridine and substituted aromatics such as sulfones, diaryl ethers, diaryl carbonyls, diaryl sulfides and the like. Aromatic compounds substituted by alkyl groups are generally not preferred for utilization in the present technique. It has been found that alkyl substituted aromatics are not only iodinated on the ring but also on the side chains. Thus, while alkyl substituted aromatics can be utilized in the present technique their use is not preferred.

The catalysts which may be employed in the present technique are described in copending applications Ser. Nos. 912,806, filed Sept. 29, 1986, 029,959 filed Mar. 25, 1987, and 029,898 filed Mar. 25, 1987. The disclosure of these applications incorporated herein by reference for a more complete description of the catalysts and reaction conditions which are to be employed.

The catalysts utilized in the present technique are generally characterized by containing non-acid sites, and more preferably basic sites. It is preferred to use zeolites with a silicon (as Si) to aluminum (as Al) ratio of 1.5 or less and a pore size greater than about 6 Å. In particular, the type of zeolites which has proven to be particularly effect is the X type. The Y type zeolite, which has a silicon to aluminum ratio of about 1.5 to 1 to 3:1, is also active for this reaction, but in the present embodiment is not preferred since a higher degree of decomposition is encountered with this catalyst. The X type zeolite is generally considered to have a silicon to aluminum ratio of 1:1 to 1.5:1, and is the preferred catalyst in this invention.

Most of the commercially available zeolites are in the sodium form; however, the alkali, alkaline earth and rare earth metal counter ions have all proven to yield useful zeolites for the transiodination of benzene. The alkali or alkaline earth metals zeolites are preferred because they exhibit greater selectivity than other cations when they are used as the counter ions. The zeolites which contain a substantially amount of the rare earth metals show a lower selectivity which is generally not desired. The counter ion is easily introduced into the zeolite by simple ion exchange and is well known to those skilled in the art. This is generally accomplished by contacting in an aqueous medium a salt of the desired counter ion and the zeolite. The period of time over which the contact is conducted and a number of times the ion exchange process is performed is dependent upon the degree of replacement which is desired. Thus, one beginning with the zeolite in the sodium form may ion exchange this material with another counter ion to partially or substantially completely replace the sodium ion with a different counter ion.

When the aromatic compound is a condensed ring aromatic such as naphthalene, it is desirable that the zeolite have been ion exchanged with sodium, potassium, rubidium and/or cesium and more preferably with potassium, rubidium of cesium. It has been found that when the zeolite is ion exchanged with lithium, calcium, strontium, barium or rare earth metals the condensed ring aromatics are decomposed to a higher degree. When the zeolite is essentially in the sodium form, decomposition of the iodonaphthalenes occur but to a lesser extent than with lithium, calcium, strontium, barium and rare earth metal counter ions. In view of the higher decomposition rate obtained when the zeolite is in the sodium form, it is preferred that the zeolite be ion exchanged with potassium, rubidium, and/or cesium such that at least 50% of the sodium ions are replaced by potassium, rubidium or cesium. However, a high degree of exchange is not necessary for the successful practice of the invention. Once more than 50% of the ion exchange groups contain potassium, rubidium or cesium excellent results are obtained. The catalyst may also contain other cations, such as oxidation metals useful for promoting the oxyiodination reaction. Oxidation metals are those metal ions capable of forming inorganic peroxides and/or which have variable valence. Suitable oxidation metals include manganese, iron, copper, cerium, chromium, vanadium, antimony, cobalt, and boron. The physical form of the catalyst is not critical and may be readily selected by the artisan. Suitable forms include pellets, beads, powders, or more complex forms.

The temperature at which the transiodination reaction is to be conducted from about 275° to 500° C., with temperatures of from 300° to 400° being preferred. Especially preferred is a temperature range from about 325° to 375° C.

The pressure at which the process is conducted is not critical and can range from subatmospheric to superatmospheric. The utilization of elevated pressures in the gas phase process may be preferred so as to minimize equipment size. In general, pressures from atmospheric to 600 psig have proven satisfactory although higher or lower pressures can be utilized. The reaction may also be carried out in the liquid phase.

The space velocity of the process is not critical and may be readily selected by the artisan. Gas hourly space velocity is between 10 and 50,000, preferably between 100 and 20,000 liters per hour of reagents per liter of active zeolite have proven satisfactory.

The catalyst is proven to have an extremely long life and degrades only slowly with time. The degradation of the catalyst is believed to be caused by the decomposition of very small quantities of the aromatic compound which deposits small quantities of carbon on the active sites thereby degrading the catalyst activity. When the reaction conditions are selected such that none of the aromatic starting material is degraded, the life of the catalyst is essentially indefinite. However, when the catalyst becomes deactivated reactivation is simple. An excellent regeneration technique comprises passing air or oxygen over the catalyst for several hours at elevated temperatures. Typically the temperature is above 400° C. although higher or lower temperatures have proven equally satisfactory. The temperature need only be high enough so as to insure combustion of the carbon deposit on the catalyst. When pure oxygen is employed lower temperatures can be utilized, while when air is employed temperatures on the order of about 400° C. have proven satisfactory.

The transiodination of iodoaromatic compounds in this fashion is quite surprising and unexpected, since the isomerization of haloaromatic compounds is considered to be a difficult process, requiring a strongly acidic catalyst and long reaction times. For example, see Olah, in *Journal of Organic Chemistry*, 27 3469 (1962).

While not being bound to any particular theory, it is believed that the ready transiodination of iodoaromatic compounds is due to the fact that reaction (I) is unique among the aromatic halogenation reactions in having a positive free energy of reaction. The equilibrium in this reaction lies strongly to the left.

$$ArH + I_2 \rightleftharpoons ArI + HI \qquad (I)$$

In the isomerization reaction, the analogous reaction (II) occurs.

$$ArH + IOAl \rightleftharpoons ArI + HOAl \qquad (II)$$

Thus, in order to accomplish the transiodination, it is necessary only to operate under conditions where some quantity of iodine and catalyst are present. This will effect deiodination according to the reverse of reaction (II) since it is an equilibrium reaction. The iodine thus freed is available for reaction and the net effect is a redistribution of iodine among the aromatic species present.

Essentially any source of iodine may be employed including elemental iodine, HI or alkyl iodides, preferably lower alkyl iodides. Furthermore, mixtures of these materials may be used as the source of iodine. If aqueous HI is employed, it is necessary to vaporize it before contacting the catalyst.

For highly reactive aromatic compounds, this redistribution reaction can occur even under oxidizing conditions, but for less reactive aromatics it is preferable to operate in the absence of oxygen to increase the concentration of HOAl in the reaction. In the presence of uniodinated species, the net effect is to decrease the concentration of di- and triiodinated compounds and increase the concentration of monoiodinated species. Preferred reactants for the transiodination reaction are optionally substituted iodobenzenes, iodobiphenyls and iodonaphthalenes. Preferably, monoiodinated and diiodinated products are produced.

The transiodination reaction can be operated as a continuous vapor phase process or can be carried out as batch or semi-batch processes if desired. When the (oxy)iodination reaction is performed as a continuous process, the transiodination reaction can be performed continuously by accepting the reaction product from an iodination reaction. One or more desired products may be isolated prior to and/or after the transiodination reaction. The remaining effluents from the transiodination reaction can be recycled and again passed through the transiodination or iodination process. A preferred embodiment is to utilize the vapor-phase transiodination reaction in conjunction with a vapor-phase oxyiodination reaction, as described in copendin application Ser. No. 912,806. When operated in this embodiment, there is very little loss of reactant materials and the products can be recycled continuously to produce any one of a number of desired isomers.

It is possible to pass the effluent from the oxyiodination reaction through several transiodination catalysts beds isolating one or more desired products after each transiodination reaction. Alternatively, the oxyiodination and transiodination reactions can be performed over the same catalyst. In this embodiment, the desired product is separated and removed after the oxyiodination and the remaining effluent from the oxyiodination which contains both undesired iosmers and unreacted compounds is mixed with incoming iodine, oxygen and aromatic starting compound and recycled through the same catalyst bed. For reactive aromatic compounds the transiodination and oxyiodination reactions will then occur simultaneously using the same catalyst bed. This embodiment eliminates the need for two separate catalyst beds which is an important economic advantage.

A further possibility is to operate the process batchwise using a single catalyst. According to this method, the oxyiodination reaction is performed, the desired product separated and removed, and the undesired isomers and unreacted compounds collected. The collected material can then be subsequently passed over the same catalyst bed to effect transiodination. When operated batchwise the transiodination reaction can be optionally run in the presence or absence of oxygen.

Obviously, it is possible to combine various aspects of these different embodiments to achieve the desired products and economic efficiency. For example, it is possible to perform the oxyiodination and transiodination reactions over the same catalyst bed and subsequently pass some portion of the effluent to a second or third transiodination catalyst bed to further redistribute the iodine among the aromatic species. This flexibility is important since it allows one to produce and isolate a number of different iodoaromatic compounds. All embodiments of the invention can be performed continuously, or as batch or semi-batch processes.

The following examples are presented to illustrate the present invention but are not intended in any way to limit the scope of the invention which is defined by the appended claims.

EXAMPLE 1

A mixture of diiodobenzene isomers obtained via oxyiodination was depleted of para-diiodobenzene by crystallization. After addition of benzene, the weight percent composition was:
  84.947% benzene
  0.095% iodobenzene
  10.784% meta-diiodobenzene
  1.725% para-diiodobenzene
  2.392% ortho-diiodobenzene Two weight percent iodine ($I_2$) was dissolved in the above mixture and was passed over 25 ml of Na-13X zeolite at 325° C. under a stream of nitrogen. The product obtained had the following composition:
  71.73% benzene
  7.45% iodobenzene
  4.39% meta-diiodobenzene
  1.424% para-diiodobenzene
  0.99% ortho-diiodobenzene The iodobenzene formed is a result of transiodination between the benzene and the diiodobenzenes.

EXAMPLE 3

Reference Example

The feed mixture of Example 1 was fed under nitrogen over a 25 ml bed of Vycor glass at 400° C. with an equal volume of 48% aqueous HI. The composition of the product was identical to the feed material, and no iodobenzene was formed.

EXAMPLE 3

Reference Example

The feed mixture of Example 1 was fed under nitrogen over a 25 ml bed of silica-alumina at 400° C. with an equal volume of 48% aqueous HI. The composition of the product was identical to the feed material, and no iodobenzene was formed.

EXAMPLE 4

Iodobenzene and 48% aqueous HI each were fed at a rate of 0.5 ml/min over 25 ml of Na-13X zeolite with an air flow of 300 ml/min at 325° C. The reaction product contained (mol %):
  40% benzene
  35% iodobenzene and
  35% diiodobenzene.

EXAMPLE 5

Naphthalene was oxyiodinated over 75 ml of Na-13X zeolite at 350° C. The reaction product was distilled under vacuum and a distillation cut was obtained with the following composition:
  0.2% naphthalene 65.2% 2-iodonaphthalene
17.3% 1-iodonaphthalene
11.8% 2,6- and 2,7-diiodonaphthalenes
5.8% other diiodonaphthalenes.

The above material was mixed with 30 wt. % iodine and was passed over the catalyst at 350° C. with 300 ml/min air flow. The reaction product had the following mol % composition:

9.4% naphthalene
37.4% 2-iodonaphthalene
25.0% 1-iodonaphthalene
19.2% 2,6- and 2,7-diiodonaphthalenes
9.0% other diiodonaphthalenes.

The formation of naphthalene demonstrates the transiodination of iodonaphthalene to naphthalene and diiodonaphthalenes under oxidizing conditions.

EXAMPLE 6

To 99% pure 1-iodonaphthalene was added 5 wt. % iodine and this mixture was fed at 0.5 ml/min over 50 cc K-X catalyst at 325° C. with 300 ml/min air flow. The reaction product had the following mol % composition:

8.4% naphthalene
12.6% 2-iodonaphthalene
70.2% 1-iodonaphthalene
8.8% diiodonaphthalenes.

Obviously, numerous modifications and variations of the present invention are possible in light of the above teachings, and that the invention may be practiced otherwise and as specifically described herein.

While the invention has been described in detail with particular reference to preferred embodiments thereof, it will be understood that variations and modifications can be effected within the spirit and scope of the invention.

We claim:

1. A process for isomerizing or transiodinating a mono-, di-, or tri-iodoaromatic compound selected from the group consisting of benzene, biphenyl, naphthalene, anthracene, thiophene, benzothiophene, pyridine and benzopyridine, comprising contacting said iodoaromatic compound with a non-acid zeolite catalyst, wherein the iodine present in said iodoaromatic compound is redistributed among the molecules of said iodoaromatic compound to form an isomerized or transiodinated product.

2. The process of claim 1 wherein said zeolite is an X-type zeolite containing alkaline or alkaline earth cations.

3. The process of claim 2, wherein said zeolite contains less than about 1 wt % of an oxidation catalyst selected from the group consisting of manganese, iron, copper, chromium, vanadium, cerium, antimony, cobalt and boron in the oxide, salt or acid form.

4. The process of claim 2 wherein said zeolite is an X-type zeolite containing potassium, rubidium or cesium cations.

5. The process of claim 1, wherein said iodoaromatic compound is an iodobenzene, iodobiphenyl or iodonaphthalene.

6. The process of claim 1 wherein said iodoaromatic compound is a product resulting from an oxyiodination reaction.

7. The process of claim 1, wherein said contacting step is conducted at a temperature from about 275°–500° C.

8. A process for iodinating an aromatic compound comprising:
(a) reacting iodine and an aromatic compound selected from the group consisting of benzene, biphenyl, naphthalene, anthracene, thiophene, benzothiophene, pyridine and benzopyridine in the presence of oxygen over a 13X type zeolite catalyst containing potassium, rubidium or cesium cations to produce a mono-, di- or tri-iodoaromatic compound and
(b) contacting said iodoaromatic compound over said zeolite catalyst, wherein the iodine present in said iodoaromatic compound is redistributed among the molecules of said iodoaromatic compound to form an isomerized or transiodinated product.

9. The process of claim 8, wherein said reacting step is conducted in the presence of $I_2$, HI or alkyl iodides.

10. The process of claim 8, wherein said reacting step is performed continuously and at least a portion of the product of said reacting step is recycled to the beginning of said reacting step.

11. The process of claim 8 wherein said contacting step is performed in the absence of oxygen.

12. The process of claim 8 wherein said aromatic compound is benzene, naphthalene or biphenyl.

13. The process of claim 1, wherein said process is conducted at a temperature from about 275°–500° C.

* * * * *